United States Patent
Bauer et al.

(10) Patent No.: US 9,777,246 B2
(45) Date of Patent: *Oct. 3, 2017

(54) COMPOUNDS, THEIR PREPARATION, AND USES

(71) Applicant: BASF SE, Ludwigshafen (DE)

(72) Inventors: Frederic Bauer, Deidesheim (DE); Rainer Eskuchen, Langenfeld (DE); Pepa Dimitrova, Worms (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/765,461

(22) PCT Filed: Feb. 26, 2014

(86) PCT No.: PCT/EP2014/053732
§ 371 (c)(1),
(2) Date: Aug. 3, 2015

(87) PCT Pub. No.: WO2014/146875
PCT Pub. Date: Sep. 25, 2014

(65) Prior Publication Data
US 2015/0368588 A1 Dec. 24, 2015

(30) Foreign Application Priority Data
Mar. 22, 2013 (EP) .................... 13160618

(51) Int. Cl.
| | | |
|---|---|---|
| C11D 1/825 | (2006.01) | |
| C11D 3/22 | (2006.01) | |
| B08B 3/04 | (2006.01) | |
| C07H 1/00 | (2006.01) | |
| C07H 3/02 | (2006.01) | |
| C07H 3/04 | (2006.01) | |
| C07H 3/06 | (2006.01) | |
| C11D 1/66 | (2006.01) | |
| C07H 15/04 | (2006.01) | |

(52) U.S. Cl.
CPC ............... *C11D 1/662* (2013.01); *C07H 1/00* (2013.01); *C07H 3/02* (2013.01); *C07H 3/04* (2013.01); *C07H 3/06* (2013.01); *C07H 15/04* (2013.01)

(58) Field of Classification Search
CPC .. C11D 1/825; C11D 3/22; B08B 3/04; C07H 1/00; C07H 3/02; C07H 3/04; C07H 3/06
See application file for complete search history.

(56) References Cited

U.S. PATENT DOCUMENTS

| | | | |
|---|---|---|---|
| H000171 H | * | 12/1986 | McDaniel ............. C11D 1/662 510/470 |
| 5,644,041 A | | 7/1997 | Johansson |
| 5,681,949 A | | 10/1997 | Johansson et al. |
| 2003/0181347 A1 | * | 9/2003 | Johansson ............. A61K 8/068 510/417 |
| 2013/0303430 A1 | | 11/2013 | Reinoso Garcia et al. |

FOREIGN PATENT DOCUMENTS

| | | | | |
|---|---|---|---|---|
| WO | WO 94/21655 | * | 9/1994 | ............. C07H 15/04 |
| WO | WO 94/21769 | | 9/1994 | |
| WO | WO 01/90286 | | 11/2001 | |
| WO | WO 2014/146958 | | 9/2014 | |

OTHER PUBLICATIONS

International Search Report issued Apr. 24, 2014, in PCT/EP2014/053732 filed Feb. 26, 2014.
Written Opinion of the International Searching Authority issued Apr. 24, 2014, in PCT/EP2014/053732 filed Feb. 26, 2014.
International Preliminary Report on Patentability issued Jun. 12, 2015, in PCT/EP2014/053732 filed Feb. 26, 2014.
U.S. Appl. No. 14/771,669, filed Aug. 31, 2015, Bauer et al.

* cited by examiner

*Primary Examiner* — Brian P Mruk
(74) *Attorney, Agent, or Firm* — Oblon, McClelland, Maier & Neustadt, L.L.P.

(57) ABSTRACT

The current invention is directed towards compounds of the general formula (I), wherein the integers are defined as follows: $R^1$ is $-(CH_2)nCH(CH_3)_2$, $R^2$ is $-(CH_2)_{n+2}CH(CH_3)_2$, $G^1$ selected from monosaccharides with 4 to 6 carbon atoms, x in the range of from 1.1 to 4, n is a number in the range of from zero to 3.

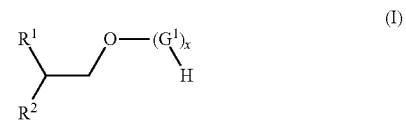

12 Claims, No Drawings

COMPOUNDS, THEIR PREPARATION, AND USES

The current invention is directed towards mixture of compounds of the general formula (I),

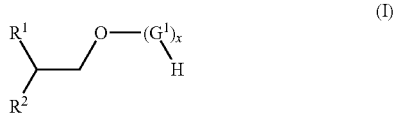

wherein the integers are defined as follows:
$R^1$ is —$(CH_2)_n CH(CH_3)_2$,
$R^2$ is —$(CH_2)_{n+2} CH(CH_3)_2$,
$G^1$ selected from monosaccharides with 4 to 6 carbon atoms,
x in the range of from 1.1 to 4,
n is a number in the range of from zero to 3.

Furthermore, the present invention is directed towards the use of compounds according to the invention, and to a process for making the compounds according to the invention. Additionally, the present invention is directed towards mixtures and aqueous formulations containing When cleaning surfaces such as hard surfaces or fibers with aqueous formulations several problems have to be solved. One task is to solubilize the dirt that is supposed to be removed and to keep it in the aqueous medium. Another task is to allow the aqueous medium to come into contact with the surface to be cleaned. A particular purpose of such hard surface cleaning can be degreasing. Degreasing as used in the context with the present invention refers to the removal of solid and/or liquid hydrophobic material(s) from a respective surface. Such solid or liquid hydrophobic material may contain additional undesired substances such as pigments and in particular black pigment(s) such as soot.

Some alkyl polyglucosides ("APG") such as described in WO 94/21655 are well known for degreasing lacquered or non-lacquered metal surfaces. When trying to apply 2-n-propylheptyl glucoside to laundry, however, it has turned out that the wetting behaviour was only unsatisfactory. In addition, the foaming behavior still can be improved since many of them develop a lot of foam quickly on occasion of agitation.

It was therefore an objective of the present invention to provide a surfactant that exhibits excellent wetting and foaming behaviour. It was further an objective to provide a method for making a compound that exhibits an excellent wetting and foaming behaviour. It was further an objective to provide a method of use of compounds that apply excellent wetting and foaming behaviour. Accordingly, the mixtures of compounds defined in the outset have been found, them being also referred to as compounds according to the invention.

Compounds according to the invention have the general formula (I),

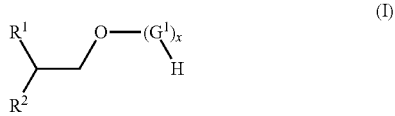

wherein the integers are defined as follows:
$R^1$ is —$(CH_2)_n CH(CH_3)_2$,
$R^2$ is —$(CH_2)_{n+2} CH(CH_3)_2$,
$G^1$ selected from monosaccharides with 4 to 6 carbon atoms,
x in the range of from 1.1 to 4, preferred are 1.1 to 2 and in particularly preferred are 1.2 to 1.8. In the context of the present invention, x refers to average values, and x is not necessarily a whole number. In a specific molecule only whole groups of $G^1$ can occur. It is preferred to determine x by High Temperature Gas Chromatography (HTLC).
n is a number in the range of from zero to 3, preferred is zero or one, and particularly preferred is zero.
$G^1$ selected from monosaccharides with 4 to 6 carbon atoms, for example tetroses, pentoses, and hexoses. Examples of tetroses are erythrose, threose, and erythulose. Examples of pentoses are ribulose, xylulose, ribose, arabinose, xylose and lyxose. Examples of hexoses are galactose, mannose and glucose. Monosaccharides may be synthetic or derived or isolated from natural products, hereinafter in brief referred to as natural saccharides or natural polysaccharides, and natural saccharides natural polysaccharides being preferred. More preferred are the following natural monosaccharides: galactose, arabinose, xylose, and mixtures of the foregoing, even more preferred are glucose, arabinose and xylose, and in particular glucose. Monosaccharides can be selected from any of their enantiomers, naturally occurring enantiomers and naturally occurring mixtures of enantiomers being preferred.

In one embodiment of the present invention, $G^1$ is selected from monosaccharides, preferably from glucose.

In single molecules of formula (I) with 2 or more monosaccharide groups, the glycosidic bonds between the monosaccharide units may differ in the anomeric configuration (α-; β-) and/or in the position of the linkage, for example in 1,2-position or in 1,3-position and preferably in 1,6-position or 1,4-position.

The integer x is a number in the range of from 1.1 to 4, preferred are 1.1 to 2 and in particularly preferred are 1.15 to 1.9. As stated before, in the context of the present invention, x refers to average values, and they are not necessarily whole numbers. Naturally, in a specific molecule only whole groups of $G^1$ can occur.

In single molecules, there may be, for example, only one $G^1$ moiety or up to 15 $G^1$ moieties per molecule.

Alkyl polyglycosides such as compound of general formula (I) are usually mixtures of various compounds that have a different degree of polymerization of the respective saccharide. It is to be understood that in formula (I), x is a number average value, preferably calculated based on the saccharide distribution determined by high temperature gas chromatography (HTGC), e.g. 400° C., in accordance with K. Hill et al., Alkyl Polyglycosides, VCH Weinheim, New York, Basel, Cambridge, Tokyo, 1997, in particular pages 28 ff., or by HPLC. If the values obtained by HPLC and HTGC are different, preference is given to the values based on HTGC.

In a particularly preferred embodiment of the present invention, in compounds according to the invention the integers are selected as follows: n is zero, x being in the range of from 1.2 to 2, and $G^1$ is glucose.

Compounds according to the invention are very good surfactants and particularly useful for hard surface cleaning. In particular, they solve the problems mentioned above.

As indicated above, x can preferably be determined by high temperature gas chromatography (HTGC), e.g. 400° C., in accordance with K. Hill et al., Alkyl Polyglycosides, VCH Weinheim, New York, Basel, Cambridge, Tokyo, 1997, in particular pages 28 ff., In one embodiment of the present invention, compounds according to the invention can have a Hazen colour number in the range of from 10 to 1,000, preferably in the range of from 50 to 800 and more preferably in the range of from 100 to 500.

The Hazen colour number can be determined according to DIN EN ISO 6271-1 or 6271-2.

In one embodiment of the present invention, compounds according to the invention can have a Gardner colour number in the range of from 0.1 to 8.0, preferably in the range of from 0.5 to 5.0 and more preferably in the range of from 1.0 to 3.5.

The Gardner colour number can be determined according to DIN EN ISO 4630-1 or 4630-2.

Both Hazen and Gardner numbers are determined based on 10% solutions.

Another aspect of the present invention is directed to mixtures comprising at least one mixture of compounds according to the invention and at least one of its isomers. Said mixtures are also being referred to as mixtures according to the invention.

Isomers preferably refer to compounds in which the sugar part is identical to $G^1$ in the particular mixture of compound according to the invention but the alkyl group is different. In one embodiment, mixtures according to the invention comprise one compound according to the invention and one compound according to formula (III),

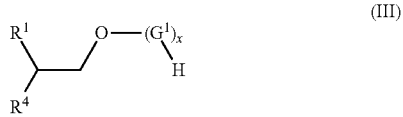

(III)

the integers being defined as follows:
$G^1$, $R^1$, x and n being identical with the respective integers of the respective compound according to the invention,
$R^4$ is —$CH_2$—$CH(CH_3)(CH_2)_{n+1}CH_3$.

In another embodiment, mixtures according to the invention comprise one compound of general formula (I) and one compound according to formula (IV),

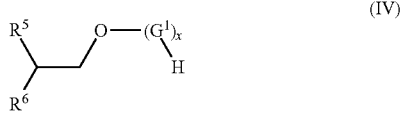

(IV)

the integers being defined as follows:
$R^5$ is —$(CH_2)_{n+1}CH_3$,
$R^6$ is —$(CH_2)_{n+3}CH_3$,
and $G^1$, x and n being identical with the respective integers of the respective compound according to the invention.

With respect to x, the same concept applies as in compounds of general formula (I).

In inventive mixtures comprising one compound of general formula (I) and one compound of general formula (III), compound of general formula (III) is preferably comprised in the range of from 1.5 to 50% by weight, referring to the whole mixture, more preferably in the range of from 3 to 40% by weight and even more preferably 5 to 25% by weight, the balance being compound of general formula (I).

In inventive mixtures comprising one compound of general formula (I) and one compound of general formula (IV), compound of general formula (IV) is preferably comprised in the range of from 0.5 to 60% by weight, referring to the whole mixture, more preferably in the range of from 1 to 30% by weight and even more preferably 1 to 20% by weight, the balance being compound of general formula (I).

Another aspect of the present invention is directed to mixtures comprising at least one compound according to the invention and at least one non-ionic surfactant selected from and at least one non-ionic surfactant, selected from alkoxylated fatty alcohols and hydroxyl-group containing non-ionic surfactants. Preferred examples of alkoxylated fatty alcohols are n-$C_yH_{2y+1}$—$O(AO)_z$—H with y being selected from whole numbers in the range from 6 to 20, AO being different or identical and selected from alkylene oxide groups such as —$CH_2CH_2O$—, —$(CH_2)_3$—$O$—, —$(CH_2)_4$—$O$—, —$CH_2CH(CH_3)$—$O$, —$CH_2CH(C_2H_5)$—$O$—, and z being selected from 3 to 50, z being an average value (number average). Another preferred example of non-ionic surfactants are hydroxyl-group containing non-ionic surfactants that are also known as hydroxyl mixed ethers (HME) such as $R^7$—CHOH—$CH_2$-$(AO)_z$—$R^8$, $R^7$ and $R^8$ being independently selected from n-$C_2$-$C_{20}$-alkyl and z and AO being as defined above.

Compounds and mixtures according to the invention are extremely useful for cleaning hard surfaces, and in particular for degreasing metal surfaces and in laundry care. If applied as aqueous formulations, they exhibit a very good foaming behaviour and wetting behaviour. In particular, compounds according to the invention and mixtures according to the invention exhibit less foam under specific conditions or at least a lesser speed of foam formation, and the foam decays fast. They can be applied with hard water, salt-free water and even with strong bases such as NaOH useful in institutional or industrial cleaning.

A further aspect of the present invention is a process for making the compound according to the invention, also being referred to as synthesis according to the invention.

The compound according to the invention can be synthesized as follows. For performing the synthesis according to the invention, it is preferred to react an alcohol of the general formula (II)

(II)

with a monosaccharide, disaccharide or polysaccharide bearing a $G^1$ group in the presence of a catalyst. $R^1$ and $R^2$ are defined in the same way as $R^1$ and $R^2$ in the respective compound of general formula (I).

In one embodiment of the present invention, the synthesis according to the invention is being carried out using a monosaccharide, disaccharide or polysaccharide or mixture of at least two of monosaccharides, disaccharides and polysaccharides as starting material. For example, in cases in which $G^1$ is glucose, glucose syrup or mixtures from glucose syrup with starch or cellulose can be used as starting material. Polymeric glucose usually requires depolymerisation before conversion with alcohol of general formula (II). It is preferred, though, to use either a monosaccharide or a disaccharide or a polysaccharide of $G^1$ as starting material, water-free or as hydrate, for example as monohydrate.

In one embodiment of the synthesis according to the invention, alcohol of the general formula (III) and monosaccharide, disaccharide or polysaccharide are selected in a molar ratio in the range of from 1.5 to 10 mol alcohol per mol monosaccharide, disaccharide or polysaccharide, preferred 2.3 to 6 mol alcohol per mol monosaccharide, disaccharide or polysaccharide, the moles of monosaccharide, disaccharide or polysaccharide being calculated on the base of the respective $G^1$ groups.

Catalysts can be selected from acidic catalysts. Preferred acidic catalysts are selected from strong mineral acids, in particular sulphuric acid, or organic acids such as sulfosuccinic acid or aryl sulfonic acids such as para-toluene sulfonic acid. Other examples of acidic acids are acidic ion exchange resins. Preferably, an amount in the range of from 0.0005 to 0.02 mol catalyst is used per mole of sugar.

In one embodiment, the synthesis according to the invention is being performed at a temperature in the range of from 90 to 125° C., preferably from 100 to 115° C., particularly preferred from 102 to 110° C.

In one embodiment of the present invention, the synthesis according to the invention is carried over a period of time in the range of from 2 to 15 hours.

During performing the synthesis according to the invention, it is preferred to remove the water formed during the reaction, for example by distilling off water. In one embodiment of the present invention, water formed during the synthesis according to the invention is removed with the help of a Dean-Stark trap. This latter embodiment is particularly preferred in embodiments where alcohol of general formula (II) and water form a low-boiling azeotropic mixture.

In one embodiment of the present invention, the synthesis according to the invention is being carried out at a pressure in the range of 20 mbar up to normal pressure.

In another embodiment, at the end of the synthesis, unreacted alcohol of the general formula (II) will be removed, e.g., by distilling it off. Such removal can be started after neutralization of the acidic catalyst with, e. g., a base such as sodium hydroxide or MgO. The temperature for distilling off the excess alcohol is selected in accordance with the alcohol of general formula (II). In many cases, a temperature in the range of from 140 to 215° C. is selected, and a pressure in the range of from 1 mbar to 500 mbar.

In one embodiment, the process according to the invention additionally comprises one or more purification steps. Possible purification steps can be selected from bleaching, e.g., with a peroxide such as hydrogen peroxide, filtering over s adsorbent such as silica gel, and treatment with charcoal.

A further aspect of is a process for making mixtures according to the invention, in brief also being referred to as mixing process according to the invention. The mixing process according to the invention can be carried out by mixing at least one compound according to the invention with at least one of its isomers or at least one non-ionic surfactant selected from alkoxylated fatty alcohols and hydroxyl-group containing non-ionic surfactants, in bulk or as preferably aqueous formulation.

The mixing process according to the invention can be carried out by mixing at least one compound according to the invention with at least one of its isomers as aqueous solutions at room temperature or at elevated temperature, for example at temperatures in the range of from 25 to 60° C. Aqueous formulations can be selected from aqueous dispersions and aqueous solutions, aqueous solutions being preferred. Preferably, mixing is carried out by combining at least one aqueous formulation comprising a compound according to the invention and at least one aqueous formulation comprising of the isomers of the respective compound according to the invention.

In one embodiment of the present invention, the mixing process according to the invention is being carried out by mixing an aqueous solution comprising in the range of from 40 to 60% by weight of compound according to the invention and at least one aqueous solution comprising in the range of from 55 to 75% by weight of its isomer, at a temperature in the range of from 20 to 80° C.

A further aspect of the present invention is the use of compounds according to the invention or mixtures according to the invention for cleaning hard surfaces. A further aspect of the present invention is a process for cleaning hard surfaces by using a compound according to the invention or mixture according to the invention, said process also being referred to as cleaning process according to the invention. In order to perform the cleaning process according to the invention, it is possible to use any compounds according to the invention or any mixture according to the invention as such or—preferably—as aqueous formulation. In such aqueous formulations, it is preferred that they contain in the range of from 35 to 80% by weight of at least one mixture according to the invention.

Hard surfaces as used in the context with the present invention are defined as surfaces of water-insoluble and—preferably—non-swellable materials. In addition, hard surfaces as used in the context of the present invention are insoluble in acetone, white spirit (mineral turpentine), and ethyl alcohol. Hard surfaces as used in the context of the present invention preferably also exhibit resistance against manual destruction such as scratching with fingernails. Preferably, they have a Mohs hardness of 3 or more. Examples of hard surfaces are glassware, tiles, stone, china, enamel, concrete, leather, steel, other metals such as iron or aluminum, furthermore wood, plastic, in particular melamine resins, polyethylene, polypropylene, PMMA, polycarbonates, polyesters such as PET, furthermore polystyrene and PVC, and furthermore, silicium (wafers) surfaces. Particularly advantageous are formulations according to the invention when used for cleaning hard surfaces that are at least part of structured objects. In the context, such structured objects refer to objects having, e. g. convex or concave elements, notches, furrows, corners, or elevations like bumps.

Fibers as used in the context with the present invention can be of synthetic or natural origin. Examples of fibers of natural origin are cotton and wool. Examples of fibers of synthetic origin are polyurethane fibers such as Spandex® or Lycra®, polyester fibers, polyamide fibers, and glass wool. Other examples are biopolymer fibers such as viscose, and technical fibers such as GoreTex®. Fibers may be single fibers or parts of textiles such as knitwear, wovens, or nonwovens.

In order to perform the cleaning process according to the invention formulations according to the invention are being applied. Preferably, formulations according to the invention are applied in their embodiments as aqueous formulations, comprising, e. g., 10 to 99.9% by weight water. Formulations according to the invention can be dispersions, solutions, gels, or solid blocks, emulsions including microemulsions, and foams, preferred are solutions. They can be used in highly diluted form, such as 1:10 up to 1:50.

In order to perform the cleaning process according to the invention, any hard surface or fiber or arrangement of fibers can be contacted (brought into contact) with a formulation according to the invention.

When contacting hard surfaces with formulations according to the invention, formulations according to the invention can be applied at ambient temperature. In a further embodiment, formulations according to the invention can be used at elevated temperatures, such as 30 to 85° C., for examples by using a formulation according to the invention that has a temperature of 30 to 85° C., or by applying a formulation according to the invention to a preheated hard surface, e. g., preheated to 30 to 85° C.

In one embodiment, it is possible to apply a formulation according to the invention to a hard surface under normal pressure. In a further embodiment, it is possible to apply a formulation according to the invention to a hard surface under pressure, e. g., by use of a high-pressure cleaner or a pressure washer.

In one embodiment of the present invention, application duration of formulation according to the invention can be in the range of from one second up to 24 hours, preferably in the range of 30 min to 5 hours in the case of fiber cleaning and preferably one second up to 1 hour in cases of hard surface cleaning such as floor cleaning, kitchen cleaning or bathroom cleaning.

Hard surface cleaning in the context of the present invention can include removing heavy soiling, removing slight soiling and removing dust, even removing small quantities of dust.

Examples of soiling to be removed are not limited to dust and soil but can be soot, hydrocarbons, e.g., oil, engine oil, furthermore residues from food, drinks, body fluids such as blood or excrements, furthermore complex natural mixtures such as grease, and complex synthetic mixtures such as paints, coatings, and pigment containing grease.

The contacting of the hard surface with formulation according to the invention can be performed once or repeatedly, for example twice or three times.

After having performed the contacting the hard surface or fiber or arrangement of fibers with formulation according to the invention the remaining formulation according to the invention containing soil or dust will be removed. Such removal can be effected by removal of the object with the now clean hard surface from the respective formulation according to the invention or vice versa, and it can be supported by one or more rinsing step(s).

After having performed the cleaning process according to the invention, the object with the now-clean hard surface or fiber or arrangement of fibers can be dried. Drying can be effected at room temperature or at elevated temperature such as, e.g., 35 to 95° C. Drying can be performed in a drying oven, in a tumbler (especially with fibers and with fabrics), or in a stream of air having room temperature or elevated temperature such as 35 to 95° C. Freeze-drying is another option.

By performing the cleaning process according to the invention, hard surfaces and fibers can be cleaned very well. In particular, objects with structured hard surfaces can be cleaned well.

A further aspect of the present invention is directed towards aqueous formulations containing at least one compound according to the present invention, such formulations also being referred to as formulations according to the invention. Inventive formulations may contain in the range of from 0.05 to 50% by weight of at least one compound according to the present invention or of a mixture according to the present invention, preferably in the range of from 0.1 to 15% by weight and even more preferably 0.2 to 5% by weight.

In one embodiment of the present invention, formulations according to the invention can contain further organic or inorganic materials.

In one embodiment of the present invention, formulations according to the invention may further contain at least one by-product, stemming from the synthesis of the compound according to the invention.

Such by-products can be, for example, starting materials from the syntheses of the compound according to the invention such as the alcohol of formula $R^1R^2CH-CH_2-OH$. Examples of further by-products from the syntheses of the compound according to the invention are polycondensation products of monosaccharide $G^1$.

Formulations according to the invention can be solid, liquid or in the form of slurries. Preferably, formulations according to the invention are selected from liquid and solid formulations. In one embodiment, formulations according to the invention are aqueous, preferably liquid aqueous formulations.

In one embodiment of the present invention, formulations according to the invention can contain 0.1 to 90% by weight of water, based on total of the respective formulation.

In one embodiment of the present invention, formulations according to the invention have a pH value in the range of from zero to 14, preferably from 3 to 11. The pH value can be chosen according to the type of hard surface and the specific application. It is, e.g., preferred to select a pH value in the range of from 3 to 4 for bathroom or toilet cleaners. It is furthermore preferred to select a pH value in the range of from 4 to 10 for dishwashing or floor cleaners.

In one embodiment of the present invention, formulations according to the invention contain at least one active ingredient. Active ingredients can be selected from soaps, anionic surfactants, such as LAS (linear alkylbenzenesulfonate) or paraffin sulfonates or FAS (fatty alcohol sulphates) or FAES (fatty alcohol ether sulphates), furthermore acids, such as phosphoric acid, amidosulfonic acid, citric acid, lactic acid, acetic acid, other organic and inorganic acids, furthermore organic solvents, such as butyl glycol, n-butoxypropanol, especially 1-butoxy-2-propanol, ethylene glycol, propylene glycol, glycerine, ethanol, monoethanolamine, and isopropanol.

In one embodiment of the present invention, formulations according to the invention comprise at least one organic acid, selected from acetic acid, citric acid, and methane sulfonic acid.

In one embodiment of the present invention, formulations according to the invention contain at least one or more active ingredients selected from non-ionic surfactants which are different from compounds of formulae (I) and (III). Examples of suitable non-ionic surfactants are alkoxylated n-$C_{12}$-$C_{20}$-fatty alcohols, such as n-$C_{10}$-$C_{20}$-alkyl(EO)$_m$OH with m being in the range of from 5 to 100, furthermore block copolymers of ethylene oxide and propylene oxide, such as poly-EO-poly-PO-poly-EO with $M_w$ in the range of from 3,000 to 5,000 g/mol PO content of from 20 to 50% by mass, furthermore alkyl polyglycosides, preferably branched $C_8$-$C_{10}$-alkyl polyglucosides, especially $C_8$-$C_{10}$-alkyl polyglucosides with a branching in 2-position of the respective $C_8$-$C_{10}$-alkyl group.

In one embodiment of the present invention, formulations according to the invention can be used as bath cleaners, as sanitary cleaners, as kitchen cleaners, as toilet cleaners, as toilet bowl cleaners, as sanitary descalers, as all-purpose household cleaners, as all-purpose household cleaner concentrates, as metal degreasers, as all purpose-household spray cleaners, as hand dish cleaners, as automatic dishwashing agents, or floor cleaners, as hand cleaners.

In one embodiment of the present invention, formulations according to the invention can contain at least one biocide or preservative, such as benzalkonium chlorides.

In another embodiment of the present invention, formulations according to the invention can be used as laundry detergents.

In one embodiment of the present invention, formulations according to the invention can contain one or more active ingredients selected from inorganic builders such as phosphates, such as triphosphates.

Phosphate-free formulations according to the present invention are preferred. In the context of the present invention, the term "phosphate-free" refers to formulations with 0.5% by weight of phosphate maximum, based on the total solids content and measured by gravimetric methods, and phosphate-free formulations can contain a minimum of 50 ppm (weight) phosphate or less.

Examples of preferred inorganic builders are silicates, silicates, carbonates, and alumosilicates. Silicates and alumosilicates can be selected from crystalline and amorphous materials.

In one embodiment of the present invention, inorganic builders are selected from crystalline alumosilicates with ion-exchanging properties, such as, in particular, zeolites. Various types of zeolites are suitable, in particular zeolites A, X, B, P, MAP and HS in their Na form or in forms in which Na is partially replaced by cations such as $Li^+$, $K^+$, $Ca^{2+}$, $Mg^{2+}$ or ammonium.

Suitable crystalline silicates are, for example, disilicates and sheet silicates. Crystalline silicates can be used in the form of their alkali metal, alkaline earth metal or ammonium salts, preferably as Na, Li or Mg silicates.

Amorphous silicates, such as, for example, sodium metasilicate, which has a polymeric structure, or Britesil® H2O (manufacturer: Akzo) can be selected.

Suitable inorganic builders based on carbonate are carbonates and hydrogencarbonates. Carbonates and hydrogencarbonates can be used in the form of their alkali metal, alkaline earth metal or ammonium salts. Preferably, Na, Li and Mg carbonates or hydrogencarbonates, in particular sodium carbonate and/or sodium hydrogencarbonate, can be selected. Other suitable inorganic builders are sodium sulphate and sodium citrate.

In one embodiment of the present invention, formulations according to the invention can contain at least one organic complexing agent (organic cobuilders) such as EDTA (N,N,N',N'-ethylenediaminetetraacetic acid), NTA (N,N,N-nitrilotriacetic acid), MGDA (2-methylglycine-N,N-diacetic acid), GLDA (glutamic acid N,N-diacetic acid), and phosphonates such as 2-phosphono-1,2,4-butanetricarboxylic acid, aminotri(methylenephosphonic acid), 1-hydroxyethylene(1,1-diphosphonic acid) (HEDP), ethylenediaminetetramethylenephosphonic acid, hexamethylenediaminetetramethylenephosphonic acid and diethylenetriaminepentamethylenephosphonic acid and in each case the respective alkali metal salts, especially the respective sodium salts. Preferred are the sodium salts of HEDP, of GLDA and of MGDA.

In one embodiment of the present invention, formulations according to the invention can contain one or more active ingredients selected from organic polymers, such as polyacrylates and copolymers of maleic acid-acrylic acid.

In one embodiment of the present invention, formulations according to the invention can contain one or more active ingredients selected from alkali donors, such as hydroxides, silicates, carbonates.

In one embodiment of the present invention, formulations according to the invention can contain one or more further ingredients such as perfume oils, oxidizing agents and bleaching agents, such as perborates, peracids or trichloroisocyanuric acid, Na or K dichloroisocyanurates, and enzymes.

Most preferred enzymes include lipases, amylases, cellulases and proteases. In addition, it is also possible, for example, to use esterases, pectinases, lactases and peroxidases.

Enzyme(s) may be deposited on a carrier substance or be encapsulated in order to protect them from premature decomposition.

In one embodiment of the present invention, formulations according to the invention can contain one or more active ingredients such as graying inhibitors and soil release polymers.

Examples of suitable soil release polymers and/or graying inhibitors are:

Polyesters of polyethylene oxides and ethylene glycol and/or propylene glycol as diol component(s) with aromatic dicarboxylic acids or combinations of aromatic and aliphatic dicarboxylic acids as acid component(s), polyesters of aromatic dicarboxylic acids or combinations of aromatic and aliphatic dicarboxylic acids as acid component(s) with di- or polyhydric aliphatic alcohols as diol component(s), in particular with polyethylene oxide, said polyesters being capped with polyethoxylated $C_1$-$C_{10}$-alkanols.

Further examples of suitable soil release polymers are amphiphilic copolymers, especially graft copolymers of vinyl esters and/or acrylic esters onto polyalkylene oxides. Further examples are modified celluloses such as, for example, methylcellulose, hydroxypropylcellulose and carboxymethylcellulose.

In one embodiment of the present invention, formulations according to the invention can contain one or more active ingredients selected from dye transfer inhibitors, for example homopolymers and copolymers of vinylpyrrolidone, of vinylimidazole, of vinyloxazolidone or of 4-vinylpyridine N-oxide, each having average molar masses $M_w$ of from 15,000 to 100,000 g/mol, and crosslinked finely divided polymers based on the above monomers.

In one embodiment of the present invention, formulations according to the invention contain 0.1 to 50% by weight, preferably 1 to 20% by weight organic complexing agent, based on the total solids content of the respective formulation according to the invention.

In one embodiment of the present invention, formulations according to the invention contain 0.1 to 80% by weight, preferably 5 to 55% by weight anionic surfactant, based on the total solids content of the respective formulation according to the invention.

In one embodiment of the present invention, formulations according to the invention can contain one or more active ingredients selected from defoamers. Examples of suitable defoamers are silicon oils, especially dimethyl polysiloxanes which are liquid at room temperature, without or with silica particles, furthermore microcrystalline waxes and glycerides of fatty acids.

In one embodiment of the present invention, formulations according to the invention do not contain any defoamer which shall mean in the context of the present invention that said formulations according to the invention comprise less than 0.1% by weight of silicon oils and less than 0.1% by weight of glycerides of fatty acids and less than 0.1% by weight of microcrystalline waxes, referring to the total solids content of the respective formulation according to the invention. In the extreme, formulations according to the invention do not contain any measureable amounts of silicon oils or glycerides of fatty acids at all.

WORKING EXAMPLES

General Remarks

Percentages are % by weight (wt %) unless expressly noted otherwise.

All measurements with respect to colour number were performed on a 10% by volume diluted paste or solution, respectively. For dilution, a 15% by volume aqueous solution of isopropanol was used.

The lab plant for producing compounds according to the invention consisted of a jacketed 4 l glass reactor, a condenser with a Dean-Stark trap, a three stage agitator, a distillation receiver and a dropping funnel. The pressure was set with a vacuum system consisting of a vacuum pump, a pressure indicator, a pressure controller and two cold traps cooled with liquid nitrogen.

To remove the excess alcohol by distillation, a 2 l round flask equipped with a stirrer, a PT 100, a Claisen distillation head, a cooler, a distillate receiver, a pressure measurement and a vacuum pump were used.

I. Synthesis of Compounds According to the Invention

As alcohol (II.1), the following compound was used:

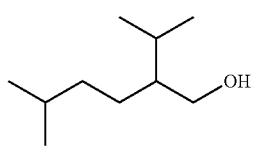

(II.1)

It was obtained by a Guerbet reaction of iso-amyl alcohol. It had an impurity of 10 mol-% of (II.1a)

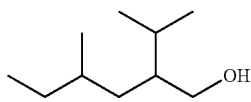

(II.1 a)

It was thus a 9:1 mixture of isomers hereinafter also being referred to as "alcohol mixture (II.1)".

I.1 Synthesis of Inventive Compound (1.1)

The 4 l glass reactor of the lab plant described above was charged with 703.6 g (2.4 moles) of glucose monohydrate and 1250 g of alcohol mixture (II.1). The resultant slurry was dried at 75° C. at a pressure of 30 mbar for a period of 30 minutes under stirring. Then, the pressure was adjusted to ambient pressure, and the slurry was heated to 90° C. An amount of 2.14 g of concentrated sulfuric acid (96% by weight), dissolved in 100 g of alcohol mixture (II.1), was added and heating was continued until a temperature of 106° C. was reached. The pressure was set to 30 mbar, and, under stirring, the water formed was distilled off at the Dean-Stark trap equipped with cold traps. After 5.5 hours, no more water was formed, and the amount of water to be formed theoretically was in the cold traps.

The reaction was then quenched by neutralizing the catalyst with 2.6 g of 50% by weight aqueous NaOH. The pH value, measured in a 10% solution in isopropanol/water (1:10), was at least 9.5. The reaction mixture was then transferred into a round flask, excess alcohol mixture (II.1) was distilled off at 140° C./1 mbar. During the removal of the excess alcohol mixture (II.1), the temperature was step-wise raised to 180° C. within 2 hours. When no more alcohol would distil off, the liquid reaction mixture was stirred into water (room temperature) in order to adjust the solids content to 60% and cooled to ambient temperature, hereby forming an aqueous paste. The compound I.1 had a degree of polymerization (number average) of 1.31 and a residual alcohol content of 0.04 g, and the paste so obtained had a water content of 40.8%. The pH value was 4.1, the colour number (Gardner) was 16.3.

In order to improve the colour, 800 g of the above aqueous paste were transferred into a 4 l vessel and reacted with 38.5 g of 35% by weight aqueous $H_2O_2$ which was added in a way that the total peroxide content was in the range of from 300 to 1,500 ppm, determined with Merckoquant peroxide test sticks. The pH value was maintained in the range from 7.5 to 8. Finally, the pH value was adjusted to 11.5 with 50% by weight aqueous NaOH. The colour number (Gardner) had dropped to 2.9, and the water content had raised to 45.9%. All measurements with respect to pH value and peroxide content were performed on a 10% by volume diluted paste. For dilution, a 15% by volume aqueous solution of isopropanol was used.

I.2 Synthesis of Inventive Compound (I.2)

The 4 l glass reactor described above was charged with 839.9 g (4.66 moles) of xylose and 1,511 g of alcohol mixture (II.1). The resultant slurry heated to 90° C. An amount of 2.55 g of concentrated sulfuric acid (96% by weight), dissolved in 100 g of alcohol mixture (II.1), was added and heating was continued until a temperature of 106° C. was reached. The pressure was set to 30 mbar, and, under stirring, the water formed was distilled off at the Dean-Stark trap equipped with cold traps. After 255 minutes, no more water was formed, and the amount of water to be formed theoretically was in the cold traps.

The reaction was then quenched by neutralizing the catalyst with 3.51 g of 50% by weight aqueous NaOH. The pH value, measured in a 10% solution in isopropanol/water (1:10), was at least 9.5. The reaction mixture was then transferred into a round flask, and at 140° C./1 mbar, excess alcohol mixture (II.1) was distilled off. During the removal of the excess alcohol mixture (II.1), the temperature was step-wise raised to 165° C. within 2 hours. When no more alcohol would distil off, the liquid reaction mixture was stirred into water (room temperature) in order to adjust the solids content to 60% and cooled to ambient temperature, hereby forming an aqueous paste. The compound 1.2 had a degree of polymerization (number average) of 1.32 and a residual alcohol content of 0.2 g, and the paste so obtained had a water content of 50.6%. The pH value was 7.8, the colour number (Gardner) was 10.1.

In order to improve the colour, 1,793 g of the above paste were transferred into a 4 l vessel and reacted with 43.3 g of 35% by weight aqueous $H_2O_2$ which was added in a way that the total peroxide content was in the range of from 300 to 1,500 ppm, determined with Merckoquant peroxide test sticks. The pH value was maintained in the range from 7.5 to 8. Finally, the pH value was adjusted to 11.5 with 50% by weight aqueous NaOH. The colour number (Gardner) had dropped to 2.5, and the water content had raised to 50.6%. All measurements with respect to pH value and peroxide content were performed on a 10% by volume diluted paste. For dilution, a 15% by volume aqueous solution of isopropanol was used.

II. Cleaning Properties of Compounds According to the Invention, and of Comparative Compounds As comparative compounds, the following compounds were used:

C-C.1: mixture of linear $C_8$-$C_{14}$-alkyl glucosides, degree of polymerization (analogue to x): 1.5, molar quantities: n-$C_8$-glucosides: 45 mole-%, n-$C_{10}$-glucosides: 50 mole-%, n-$C_{12}$-glucosides: 3 mole-%, n-$C_{14}$-glucosides: 2 mole-%

C-C.2: 2-ethylhexyl glucoside, degree of polymerization (analogue to x): 1.3

C-C.3: n-$C_8$-alkyl glucoside, degree of polymerization (analogue to x): 1.3

C-C.4: n-$C_5H_{11}$—CH(n-$C_3H_7$)—$CH_2$-glucoside ("n-2PH glucoside"), degree of polymerization (analogue to x): 1.3

C-C.5: n-$C_5H_{11}$—CH(n-$C_3H_7$)—$CH_2$-xyloside ("n-2PH xyloside"), degree of polymerization (analogue to x): 1.3

Test Soil:

36 wt % white spirit (boiling range)80/110°;

17 wt % triglyceride (commercially available Myritol® 318;

40 wt % mineral oil (commercially available Nytex® 801), 7 wt % carbon black

In order to prepare the test soil, a beaker was charged with the white spirit. The triglyceride and the mineral oil were added under stirring (500 rpm) until a clear solution had formed. The carbon black was then slowly added. The dispersion so obtained was then stirred for 30 minutes with an IKA Ultra-Turrax® T25 digital-basic. Thereafter, the dispersion was then stirred with a magnetic stirrer for 21 days at ambient temperature and then for 30 minutes with the Ultra-Turrax specified above. The dispersion so obtained was then stored in a closed glass bottle for additional 14 days under ambient conditions while being continuously stirred on a magnetic stirring device. The test soil so obtained was then ready for use.

As test substrates, white PVC stripes (37·423·1.2 mm) were used, commercially available from Gerrits, PVC-Tanzteppich® 5410 Vario white.

As test cleaners, the amounts of compound according to the invention or of comparative compound according to table 1 were dissolved in 50 ml of water. The pH value was adjusted to 7 with 0.1 M NaOH or 0.1 M acetic acid, if necessary. Then, the total mass of each of the test cleaners was adjusted to the total mass of 100 g (±0.2) g by addition of distilled water.

The tests were Gardner tests performed in an automatic test robot. It contained a sponge (viscose, commercially available as Spontex® Z14700), cross section 9.4 cm. Per run, 5 test stripes were first soiled with 0.28 (±0.2) g of test soil by brush and then dried at ambient temperature for one hour. Then they were treated with the humid sponge, soaked with 20 ml of test cleaner, swaying ten times with a weight of 300 g and a swaying velocity 10 m/s, followed by rinsing twice with distilled water and drying at ambient temperature for 4 hours.

For each test stripe, a new sponge was used. The soling and de-soiling was recorded with a digital camera.

TABLE 1

Cleaning experiments with compound (I.1) and of comparative compounds

| Name | surfactant | solids content (only surfactant) [g/100 ml] | Soil removal [%] | Standard deviation [%] |
|---|---|---|---|---|
| C-HSC.1 | C-C.1 | 2 | 66.8 | 2.4 |
| HSC.2 | (I.1) | 2 | 74.1 | 1.9 |
| C-HSC.3 | C-C.2 | 2 | 53.8 | 1.8 |
| C-HSC.4 | C-C.3 | 2 | 51.9 | 3.2 |
| C-HSC.5 | C-C.1 | 4 | 64.8 | 2.4 |
| HSC.6 | (I.1) | 4 | 80.8 | 1.6 |
| C-HSC.7 | C-C.2 | 4 | 60.5 | 3.8 |
| C-HSC.8 | C-C.3 | 4 | 56.3 | 3.3 |

The solids content refers to the test cleaner and is expressed in g solids/100 g. NaOH or acetic acid content are neglected.

The standard deviation refers to the 5 PVC stripes tested per run with the same cleaner and the same soil.

II.2 Wetting Power and Foaming Power

The wetting power was tested in accordance with ISO 8022:1990, modified in accordance with EN1772:1995. The wetting power is expressed in seconds and means the time necessary for wetting a cotton swatch in a beaker filled with aqueous solution of the respective surfactant until it sinks to the bottom of the beaker. The shorter the time the higher is the wetting power. As laundry cleaners ("LCW"), aqueous solutions consisting of 1 g/l of respective surfactant (±0.02 g) in distilled water were applied.

As substrates, TNV30 Cotton Swatches, diameter 30 mm (Immersion) according to DIN ISO 8022 (wfk-Testgewebe GmbH) were applied.

The temperature was constant in a range of ±2° C.

The foaming power was determined according to EN12728/DIN 53902 at 40° C. with water of 10° dH (German hardness). As laundry cleaners ("LCF"), aqueous solutions consisting of 2 g/l of respective surfactant (±0.02 g) in distilled water were applied. The temperature was kept constant in a range of ±2° C.

The results are summarized in tables 2a and 2b.

TABLE 2a

Wetting power

| Name | surfactant | Wetting power at 23° C. [s] | Wetting power at 70° C. [s] |
|---|---|---|---|
| LCW.2 | (I.1) | 72 | 73 |
| C-LCW.3 | C-C.4 | 80 | 88 |
| LCW.4 | (I.2) | 2 | 3 |
| C-LCW.5 | C-C.5 | 10 | 7 |
| C-LCW.2 | C-C.2 | >300 | >300 |

It can be seen that the polyglucoside based on reaction products of alcohol mixture (II.1) is superior over polyglucoside based on 2-n-propylheptanol with respect to the wetting power, and that the polyxyloside based on reaction products of alcohol mixture (II.1) is superior the respective polyxyloside based on 2-n-propylheptanol. Polyxylosides, however, have a higher price than polyglucosides and are therefore not accepted in all applications.

TABLE 2b

Foaming power

| Name | surfactant | Foaming power at 40° C. [ml] |
| --- | --- | --- |
| C-LCF.1 | C-C.1 | 660 |
| LCF.2 | (I.1) | 140 |
| C-LCF.3 | C-C.4 | 620 |
| LCF.4 | (I.2) | 90 |
| C-LCF.5 | C-C.5 | 100 |
| C-LCF.2 | C-C.2 | 110 |

The experimental error in determining the foaming power is less than ±5%. It can be seen that the polyglucoside based on reaction products of alcohol mixture (II.1) is superior over polyglucoside based on 2-n-propylheptanol with respect to the foaming power, and that the polyxyloside based on reaction products of alcohol mixture (II.1) is superior the respective polyxyloside based on 2-n-propylheptanol.

II.3 Foam Stability Tests

The experiments for determination of the foam stability were carried out in a Sita Foam Tester R-2000. As test solutions, aqueous solutions of 1 g/l of the respective polyglycoside in distilled water were used. An amount of 300 ml of the respective test solution was pumped into a glass vessel and heated to the respective temperature. Then it was stirred for 1 minute at 1,500 rpm. Then the volume of the foam was determined. Stirring and measuring was repeated 9 times. The stirrer was then set off, and the decay of the foam was determined. Measurements 10 minutes after set-off are in Table 3 or 3a or 3b, respectively. The results are summarized in Table 3. For Table 3a, the experiments were repeated but water with 16° dH (German hardness) was used instead of distilled water. For Table 3b, the experiments were repeated but 1% by weight aqueous NaOH solution was used instead of distilled water.

TABLE 3

Results of the foam stability tests in distilled water

| Surfactant | Temperature [° C.] | Maximum foam volume [ml] | Reached after time [min] | Foam volume 10 minutes after stirrer set-off [ml] |
| --- | --- | --- | --- | --- |
| (I.1) | 20 | 375 | 8 | 250 |
| C-C.4 | 20 | 957 | 9 | 865 |
| (I.2) | 20 | 932 | 10 | 800 |
| C-C.5 | 20 | 901 | 3 | 826 |
| (I.1) | 40 | 814 | 4 | 16 |
| C-C.4 | 40 | 1085 | 7 | 843 |
| (I.2) | 40 | 966 | 6 | 417 |
| C-C.5 | 40 | 972 | 5 | 616 |
| (I.1) | 60 | 100 | 4 | 0 |
| C-C.4 | 60 | 1083 | 10 | 390 |
| (I.2) | 60 | 993 | 9 | 32 |
| C-C.5 | 60 | 1037 | 6 | 103 |

TABLE 3a results of the foam stability tests in water 16° dH

| Surfactant | Temperature [° C.] | Maximum foam volume [ml] | Reached after time [min] | Foam volume 10 minutes after stirrer set-off [ml] |
| --- | --- | --- | --- | --- |
| (I.1) | 20 | 237 | 8 | 51 |
| C-C.4 | 20 | 604 | 10 | 184 |
| (I.1) | 40 | 125 | 6 | 3 |
| C-C.4 | 40 | 887 | 10 | 4 |
| (I.1) | 60 | 89 | 5 | 0 |
| C-C.4 | 60 | 455 | 10 | 0 |

TABLE 3b

Results of the foam stability tests in 1% by weight aqueous NaOH

| Surfactant | Temperature [° C.] | Maximum foam volume [ml] | Reached after time [min] |
| --- | --- | --- | --- |
| (I.1) | 20 | 224 | 10 |
| C-C.4 | 20 | 888 | 7 |
| (I.1) | 40 | 141 | 2 |
| C-C.4 | 40 | 906 | 6 |
| (I.1) | 60 | 87 | 2 |
| C-C.4 | 60 | 570 | 10 |

In examples according to the invention, the foam volume was less or at least formed less fast, and the undesired foam was less stable than in the comparative examples with the respective polyglycoside part.

The invention claimed is:

1. Mixture of compounds of general formula (I)

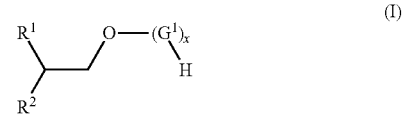

wherein:
$R^1$ is $—(CH_2)_n CH(CH_3)_2$,
$R^2$ is $—(CH_2)_{n+2} CH(CH_3)_2$,
$G^1$ selected from monosaccharides with 4 to 6 carbon atoms,
x in the range of from 1.1 to 4,
n is a number in the range of from zero to 3.

2. Mixture of compounds according to claim 1, characterized in that $G^1$ is selected from glucose, arabinose and xylose.

3. Mixture of compounds according to claim 1, characterized in that x is in the range of from 1.15 to 1.9.

4. Mixture of compounds according to claim 1, characterized in that n is zero.

5. Mixture of compounds according to claim 1, characterized in that in molecules with x being 2 or more, the saccharide groups are linked in 1,4-position(s).

6. Mixture, containing at least one mixture of compounds according to claim 1 and at least one of its isomers in which the sugar part is identical to $G^1$ but the alkyl group is different.

7. Mixture, containing at least one mixture of compounds according to claim 1 and at least one non-ionic surfactant, selected from alkoxylated fatty alcohols and hydroxyl-group containing non-ionic surfactants.

8. Process for making a mixture of compounds according to claim 1, comprising the step of reacting an alcohol of the general formula (II)

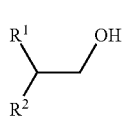 (II)

with a monosaccharide, disaccharide or polysaccharide bearing a $G^1$ group in the presence of a catalyst.

9. Aqueous formulation containing in the range of from 0.05 to 50% by weight of one mixture of compounds according to claim 1.

10. An aqueous formulation comprising from 0.05 to 50% by weight of said mixture of compounds of general formula (I) according to claim 1, and further comprising at least one by-product or starting material, stemming from the synthesis of said mixture of compounds.

11. Process for cleaning hard surfaces or fibers by contacting a hard surface or fiber or an arrangement of fibers with at least one aqueous formulation containing a mixture of compounds according to claim 1.

12. Process according to claim 11, characterized in that the cleaning comprises a degreasing.

* * * * *